(12) United States Patent
Blumenkranz

(10) Patent No.: US 9,883,920 B2
(45) Date of Patent: Feb. 6, 2018

(54) CLEANING OF A SURGICAL INSTRUMENT FORCE SENSOR

(71) Applicant: Intuitive Surgical Operations, Inc., Sunnyvale, CA (US)

(72) Inventor: Stephen J. Blumenkranz, Los Altos Hills, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 304 days.

(21) Appl. No.: 14/848,566

(22) Filed: Sep. 9, 2015

(65) Prior Publication Data

US 2015/0374447 A1 Dec. 31, 2015

Related U.S. Application Data

(60) Continuation of application No. 13/897,700, filed on May 20, 2013, now Pat. No. 9,192,448, which is a
(Continued)

(51) Int. Cl.
| | |
|---|---|
| *A61B 90/70* | (2016.01) |
| *A61B 34/30* | (2016.01) |
| *B08B 9/00* | (2006.01) |
| *A61B 17/00* | (2006.01) |
| *A61B 90/00* | (2016.01) |

(52) U.S. Cl.
CPC .............. *A61B 90/70* (2016.02); *A61B 34/30* (2016.02); *B08B 9/00* (2013.01); *A61B 2017/00477* (2013.01); *A61B 2034/305* (2016.02); *A61B 2090/064* (2016.02); *A61B 2090/701* (2016.02)

(58) Field of Classification Search
CPC ......... A61B 34/30; A61B 34/35; A61B 34/71; A61B 2034/305; A61B 17/00234; A61B 2017/00305; A61B 2017/00309; A61B 2017/00314; A61B 2017/00318;
(Continued)

(56) References Cited

U.S. PATENT DOCUMENTS

| | | |
|---|---|---|
| 5,807,377 A | 9/1998 | Madhani et al. |
| 6,331,181 B1 | 12/2001 | Tierney et al. |

(Continued)

FOREIGN PATENT DOCUMENTS

WO   WO-2007120329 A2   10/2007

OTHER PUBLICATIONS

U.S. Appl. No. 60/755,108, filed Dec. 30, 2005, Blumenkranz, Stephen J. et al.
(Continued)

*Primary Examiner* — Sarah W Aleman

(57) ABSTRACT

A force transducer is coupled to a distal portion of a shaft of a surgical instrument. The force transducer includes proximal and distal portions, radial ribs, and a plurality of strain gauges. The radial ribs form a plurality of through passages. The surgical instrument further includes a flush manifold that receives a liquid from a proximal portion of the shaft, and that directs the liquid along a first subset of through passages of the plurality of through passages toward the distal portion of the force transducer. A plenum at the distal portion of the force transducer collects the liquid from the first subset of through passages and redirects the liquid back toward the proximal portion of the shaft along a second subset of through passages of the plurality of through passages different from the first subset of through passages.

16 Claims, 18 Drawing Sheets

Related U.S. Application Data division of application No. 12/468,618, filed on May 19, 2009, now Pat. No. 8,465,474.

(58) Field of Classification Search
CPC ........... A61B 2017/00323; A61B 2017/00477; A61B 90/70; A61B 90/701
See application file for complete search history.

(56) References Cited

U.S. PATENT DOCUMENTS

| | | |
|---|---|---|
| 6,371,952 B1 | 4/2002 | Madhani et al. |
| 6,491,701 B2 | 12/2002 | Tierney et al. |
| 6,574,355 B2 | 6/2003 | Green |
| 6,676,684 B1 | 1/2004 | Morley et al. |
| 6,770,081 B1 | 8/2004 | Cooper et al. |
| 6,783,524 B2 | 8/2004 | Anderson et al. |
| 6,817,974 B2 | 11/2004 | Cooper et al. |
| 6,866,671 B2 | 3/2005 | Tierney et al. |
| 6,879,880 B2 | 4/2005 | Nowlin et al. |
| 6,902,560 B1 | 6/2005 | Morley et al. |
| 6,936,042 B2 | 8/2005 | Wallace et al. |
| 6,994,708 B2 | 2/2006 | Manzo |
| 8,465,474 B2 | 6/2013 | Blumenkranz |
| 2005/0200324 A1 | 9/2005 | Guthart et al. |
| 2006/0161138 A1 | 7/2006 | Orban, III |
| 2007/0137371 A1 | 6/2007 | Devengenzo et al. |
| 2007/0151390 A1 | 7/2007 | Blumenkranz et al. |
| 2007/0151391 A1 | 7/2007 | Larkin et al. |
| 2009/0157092 A1 | 6/2009 | Blumenkranz et al. |
| 2010/0250000 A1 | 9/2010 | Blumenkranz et al. |
| 2013/0306112 A1 | 11/2013 | Blumenkranz |

OTHER PUBLICATIONS

U.S. Appl. No. 60/755,157, filed Dec. 30, 2005, Larkin, David Q.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

CLEANING OF A SURGICAL INSTRUMENT FORCE SENSOR

This application is continuation of U.S. patent application Ser. No. 13/897,700 (filed May 20, 2013), which is a divisional of U.S. patent application Ser. No. 12/468,618 (filed May 19, 2009), now U.S. Pat. No. 8,465,474 B2, each of which is incorporated herein by reference.

CROSS-REFERENCE TO RELATED APPLICATIONS AND PATENTS

This application is related to U.S. Provisional Application No. 60/755,108 filed Dec. 30, 2005, U.S. Provisional Application 60/755,157 filed Dec. 30, 2005, U.S. patent application Ser. No. 11/958,772 filed Dec. 18, 2007, U.S. application Ser. No. 11/553,303 filed Oct. 26, 2006, U.S. patent application Ser. No. 11/537,241 filed Sep. 29, 2006, U.S. patent application Ser. No. 11/093,372 filed Mar. 30, 2005, and U.S. Pat. Nos. 6,936,042, 6,902,560, 6,879,880, 6,866,671, 6,817,974, 6,783,524, 6,676,684, 6,371,952, 6,331,181, and 5,807,377, the full disclosures of which are incorporated by reference herein for all purposes.

TECHNICAL FIELD

The present invention relates generally to surgical robot systems and, more particularly, to an improved system, apparatus, and method for cleaning a surgical instrument.

BACKGROUND

In robotically-assisted surgery, the surgeon typically operates a master controller to control the motion of surgical instruments at the surgical site from a location that may be remote from the patient (e.g., across the operating room, in a different room or a completely different building from the patient). The master controller usually includes one or more hand input devices, such as handheld wrist gimbals, joysticks, exoskeletal gloves, handpieces, or the like, which are operatively coupled to the surgical instruments through a controller with servo motors for articulating the instruments' position and orientation at the surgical site. The servo motors are typically part of an electromechanical device or surgical manipulator arm ("the slave") that includes a plurality of joints, linkages, etc., that are connected together to support and control the surgical instruments that have been introduced directly into an open surgical site or through trocar sleeves (cannulas) inserted through incisions into a body cavity, such as the patient's abdomen. There are available a variety of surgical instruments, such as tissue graspers, needle drivers, electrosurgical cautery probes, etc., to perform various functions for the surgeon, e.g., retracting tissue, holding or driving a needle, suturing, grasping a blood vessel, dissecting, cauterizing, coagulating tissue, etc. A surgeon may employ a large number of different surgical instruments/tools during a procedure.

This new surgical method through remote manipulation has created many new challenges. One such challenge is providing the surgeon with the ability to accurately "feel" the tissue that is being manipulated by the surgical instrument via the robotic manipulator. The surgeon must rely on visual indications of the forces applied by the instruments or sutures. It is desirable to sense the forces and torques applied to the tip of the instrument, such as an end effector (e.g., jaws, grasper, blades, etc.) of robotic minimally invasive surgical instruments, in order to feed the forces and torques back to the surgeon user through the system hand controls or by other means, such as visual display, vibrations, or audible tone. One device for this purpose from the laboratory of G. Hirzinger at DLR Institute of Robotics and Mechatronics is described in "Review of Fixtures for Low-Invasiveness Surgery" by F. Cepolina and R. C. Michelini, *Int'l Journal of Medical Robotics and Computer Assisted Surgery*, Vol. 1, Issue 1, page 58, the contents of which are incorporated by reference herein for all purposes. However, that design disadvantageously places a force sensor distal to (or outboard of) the wrist joints, thus requiring wires or optic fibers to be routed through the flexing wrist joint and also requiring the yaw and grip axes to be on separate pivot axes.

Another problem has been fitting and positioning the necessary wires, rods, or tubes for mechanical actuation of end effectors in as small a space as possible because relatively small instruments are typically desirable for performing surgery.

Yet another problem has been cleaning and/or sterilizing the surgical instrument after use or prior to reuse, especially in light of constraints on how a liquid may flow to reach the distal tip of an instrument force sensor and ensure adequate flushing and cleaning of the instrument.

Improved telerobotic systems and methods for remotely controlling surgical instruments at a surgical site on a patient are therefore desirable. In particular, systems, instruments, and methods should be configured to provide accurate feedback of forces and torques to the surgeon to improve user awareness and control of the instruments, while also providing for the cleaning of a reusable force sensing instrument after use or prior to reuse.

SUMMARY

The present invention provides an apparatus, system, and method for improving force and torque feedback to and sensing by a surgeon performing a robotic surgery while also providing for the cleaning of a reusable force sensing instrument.

In one embodiment, a force sensing robotic surgical instrument includes a proximal housing linkable with a surgical robot arm, a shaft having a proximal portion and a distal portion, the proximal portion operably coupled to the housing, and a force transducer operably coupled to the distal portion of the shaft, the force transducer having a proximal portion, a distal portion, a plurality of radial ribs, and a strain gauge positioned over each of the plurality of radial ribs, the radial ribs forming a plurality of through passages. The instrument further includes a wrist mechanism coupled to the distal portion of the force transducer, an end effector coupled to the wrist mechanism, and a flush manifold that receives a liquid from the proximal portion of the shaft and directs the liquid along a first subset of through passages of the force transducer toward the distal portion of the force transducer. A plenum at the distal portion of the force transducer collects the liquid from the first subset of through passages and redirects the liquid back toward the proximal portion of the shaft along a second subset of through passages different from the first subset of through passages.

In another embodiment, a surgical instrument is similar to that described above but the force transducer has a proximal portion, a distal portion, a centerline through passage running along a centered lengthwise axis of the force transducer, a plurality of radial ribs extended from the centerline through passage, and a strain gauge positioned over each of the plurality of radial ribs, the radial ribs forming a plurality of through passages. The instrument further includes a flush manifold that receives a liquid from the proximal portion of the shaft and directs the liquid along the centerline through passage of the force transducer, and a plenum at the distal portion of the force transducer that collects the liquid from the centerline through passage and redirects the liquid back toward the proximal portion of the shaft along the plurality of through passages.

In yet another embodiment, a method of cleaning a force sensing surgical instrument includes flowing a cleaning liquid through a flush manifold at a distal portion of an instrument shaft, directing the liquid along passages coupled to the flush manifold toward a distal portion of a force transducer, collecting the liquid from the passages at a plenum, and redirecting the liquid back toward the proximal portion of the shaft along a plurality of linkages to clean the plurality of linkages.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Figure 1A:
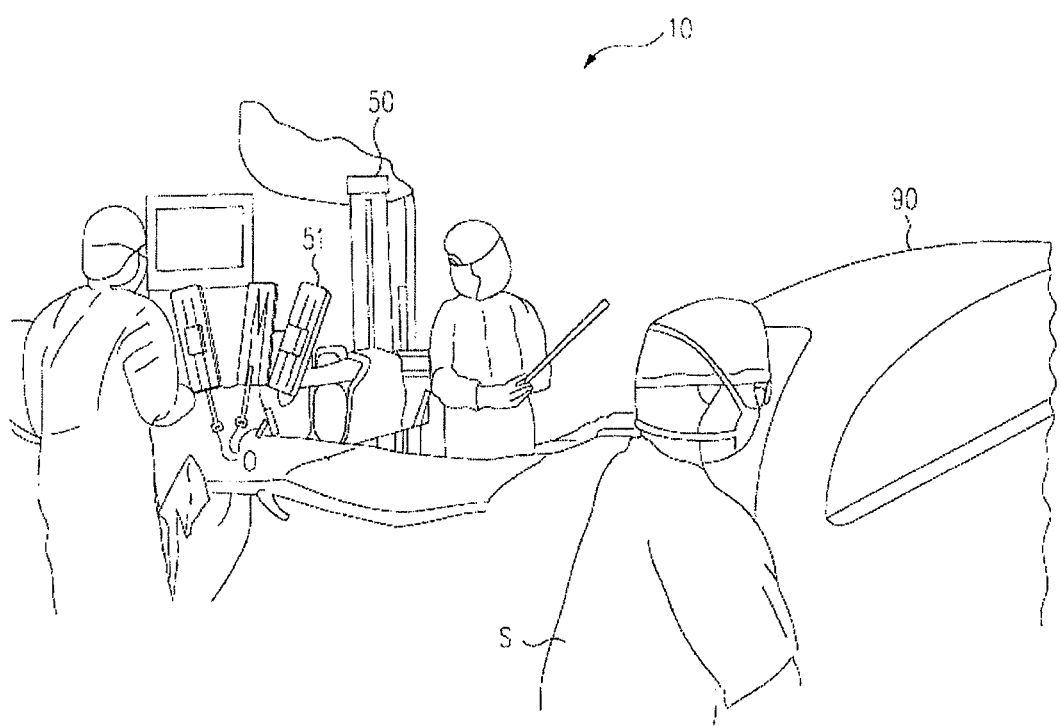
FIG. 1A is a perspective view of a robotic surgical system.
Figure 1B:
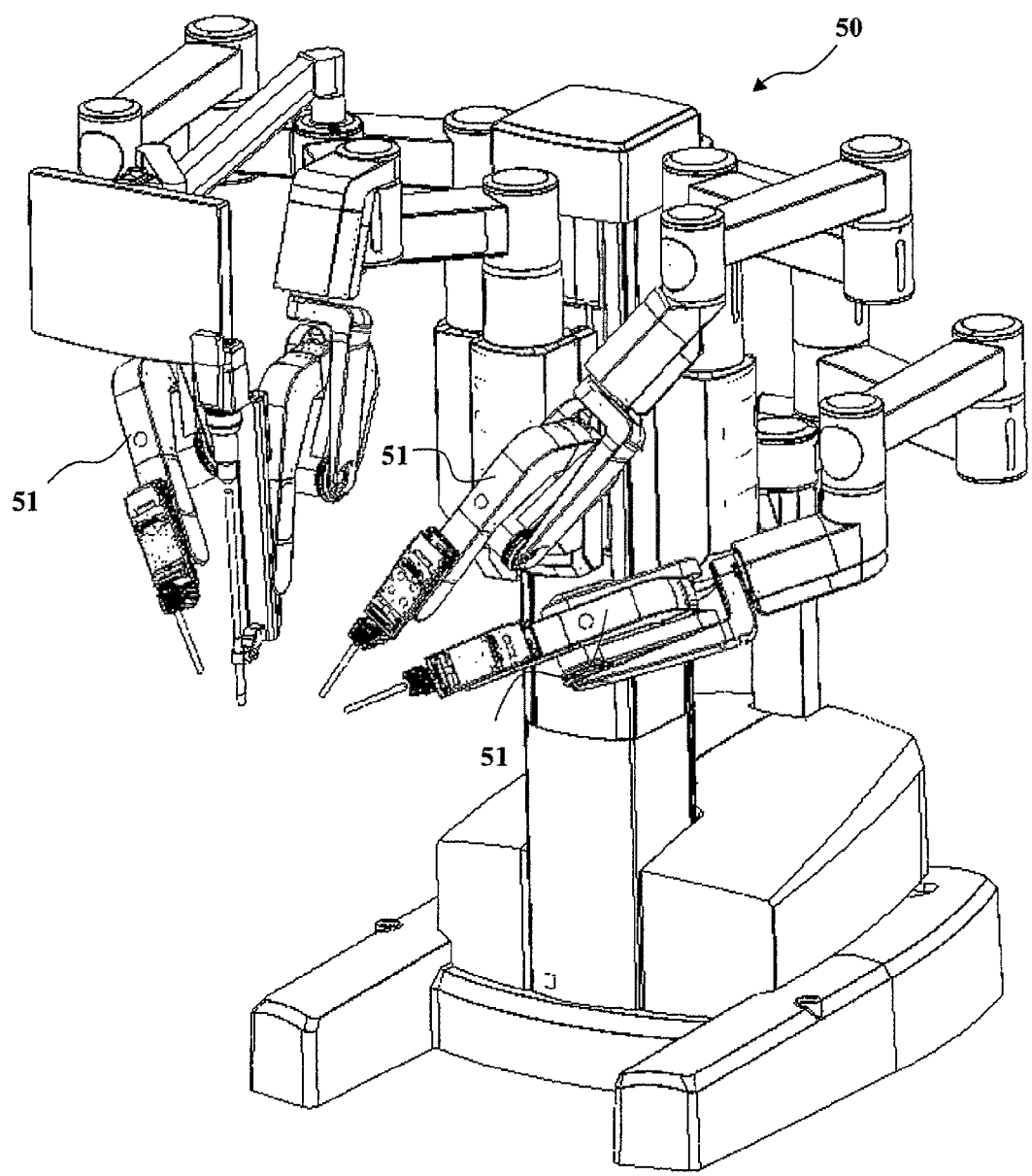
FIG. 1B is a perspective view of a robotic surgical arm cart system of the robotic surgical system in FIG. 1A.
Figure 1C:
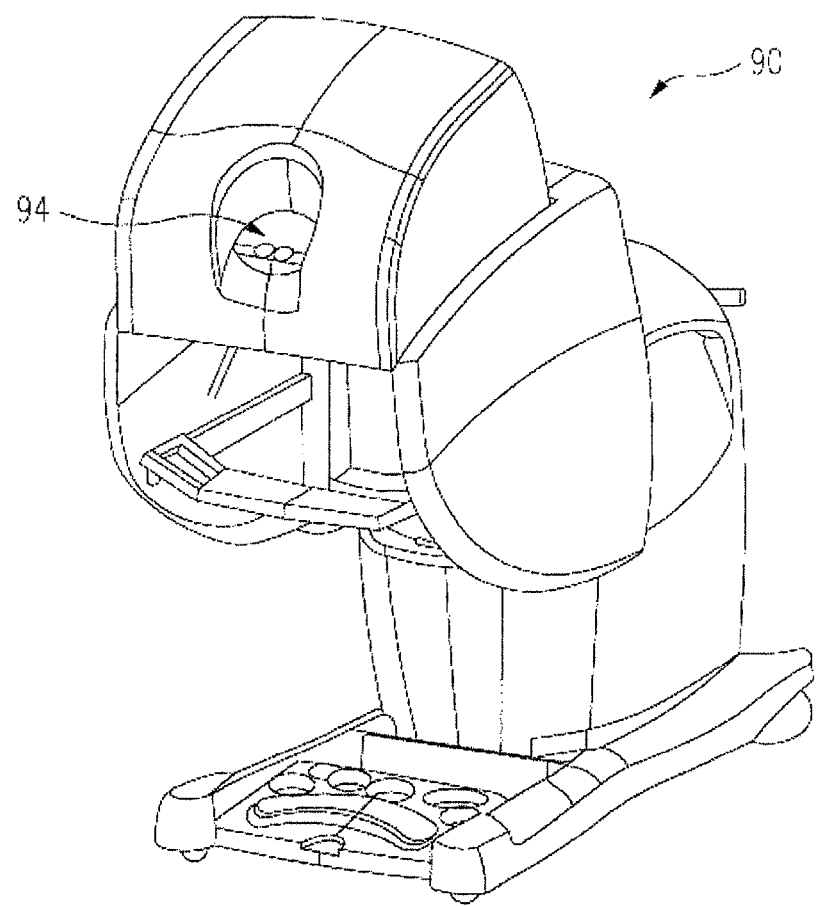
FIG. 1C is a front perspective view of a master console of the robotic surgical system in FIG. 1A.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system, apparatus, and method for sensing forces applied to tissue while performing robotically-assisted surgical procedures on a patient, particularly including open surgical procedures, neurosurgical procedures, and minimally invasive procedures, such as laparoscopy, arthroscopy, thorascopy, and the like. The apparatus and method of the present invention are particularly useful as part of a telerobotic surgical system that allows the surgeon to manipulate the surgical instruments through a servomechanism from a location remote from the patient. To that end, the combined manipulator apparatus or slave and surgical instrument of the present invention will usually be driven by a master having the same degrees of freedom (e.g., 3 degrees of freedom for position and 3 degrees of freedom for orientation plus grip) to form a telepresence system with force reflection or other scalar force magnitude display. A description of a suitable slave-master system can be found in U.S. Pat. No. 6,574,355, the complete disclosure of which is incorporated herein by reference for all purposes.

Referring to the drawings in detail, wherein like numerals indicate like elements, a robotic surgical system 10 is illustrated according to an embodiment of the present invention. As shown in FIGS. 1A through 10, robotic system 10 generally includes one or more surgical manipulator assemblies 51 mounted to or near an operating table O and a master control assembly located at a surgeon's console 90 for allowing the surgeon S to view the surgical site and to control the manipulator assemblies 51. The system 10 will also include one or more viewing scope assemblies and a plurality of surgical instrument assemblies 54 or 154 (FIGS. 2 and 5) adapted for being removably coupled to the manipulator assemblies 51 (discussed in more detail below). Robotic system 10 includes at least two manipulator assemblies 51 and preferably at least three manipulator assemblies 51. The exact number of manipulator assemblies 51 will depend on the surgical procedure and the space constraints within the operating room among other factors. As discussed in detail below, one of the assemblies 51 will typically operate a viewing scope assembly (e.g., in endoscopic procedures) for viewing the surgical site, while the other manipulator assemblies 51 operate surgical instruments 54 for performing various procedures on the patient.

The control assembly may be located at a surgeon's console 90 (FIG. 10) which is usually located in the same room as operating table O so that the surgeon may speak to his/her assistant(s) and directly monitor the operating procedure. However, it should be understood that the surgeon S can be located in a different room or a completely different building from the patient. The master control assembly generally includes a support, a monitor for displaying an image of the surgical site to the surgeon S, and one or more master(s) for controlling manipulator assemblies 51. Master(s) may include a variety of input devices, such as hand-held wrist gimbals, joysticks, gloves, trigger-guns, hand-operated controllers, voice recognition devices, or the like. Preferably, master(s) will be provided with the same degrees of freedom as the combined manipulator 51 and surgical instrument assemblies 54. In conjunction with the endoscopic view, this provides the surgeon with telepresence, the perception that the surgeon is immediately adjacent to and immersed in the surgical site, and intuitiveness, the perception that the master(s) are integral with the instruments 54 so that the surgeon has a strong sense of directly and intuitively controlling the instruments as if they are part of or held in his/her hands. Position, force, and tactile feedback sensors (not shown) may also be employed on instrument assemblies 54/154 to transmit position, force, and tactile sensations from the surgical instrument back to the surgeon's hands, ears, or eyes as he/she operates the telerobotic system. One suitable system and method for providing telepresence to the operator is described in U.S. Pat. No. 6,574,355, which has previously been incorporated herein by reference.

The monitor 94 (FIG. 10) will be suitably coupled to the viewing scope assembly such that an image of the surgical site is provided adjacent the surgeon's hands on the surgeon console. Preferably, monitor 94 will display an image that is oriented so that the surgeon feels that he or she is actually looking directly down onto the operating site. To that end, an image of the surgical instruments 54 appears to be located substantially where the operator's hands are located. In addition, the real-time image is a stereo image such that the operator can manipulate the end effector via the hand control as if viewing the workspace in substantially true presence. The image simulates the viewpoint or orientation of an operator who is physically manipulating the surgical instruments 54.

A servo control is provided for transferring the mechanical motion of masters to manipulator assemblies 51. The servo control may be separate from, or integral with, manipulator assemblies 51. The servo control will usually provide force and torque feedback from the surgical instruments 54 to the hand-operated masters. In addition, the servo control may include a safety monitoring controller (not shown) to safely halt system operation, or at least inhibit all robot motion, in response to recognized undesirable conditions (e.g., exertion of excessive force on the patient, mismatched encoder readings, etc.). The servo control preferably has a servo bandwidth with a 3 dB cut off frequency of at least 10 Hz so that the system can quickly and accurately respond to the rapid hand motions used by the surgeon and yet filter out undesirable surgeon hand tremors. To operate effectively with this system, manipulator assemblies 51 have a relatively low inertia, and the drive motors have relatively low ratio gear or pulley couplings. Any suitable conventional or specialized servo control may be used in the practice of the present invention, with those incorporating force and torque feedback being particularly preferred for telepresence operation of the system.

Figure 2:
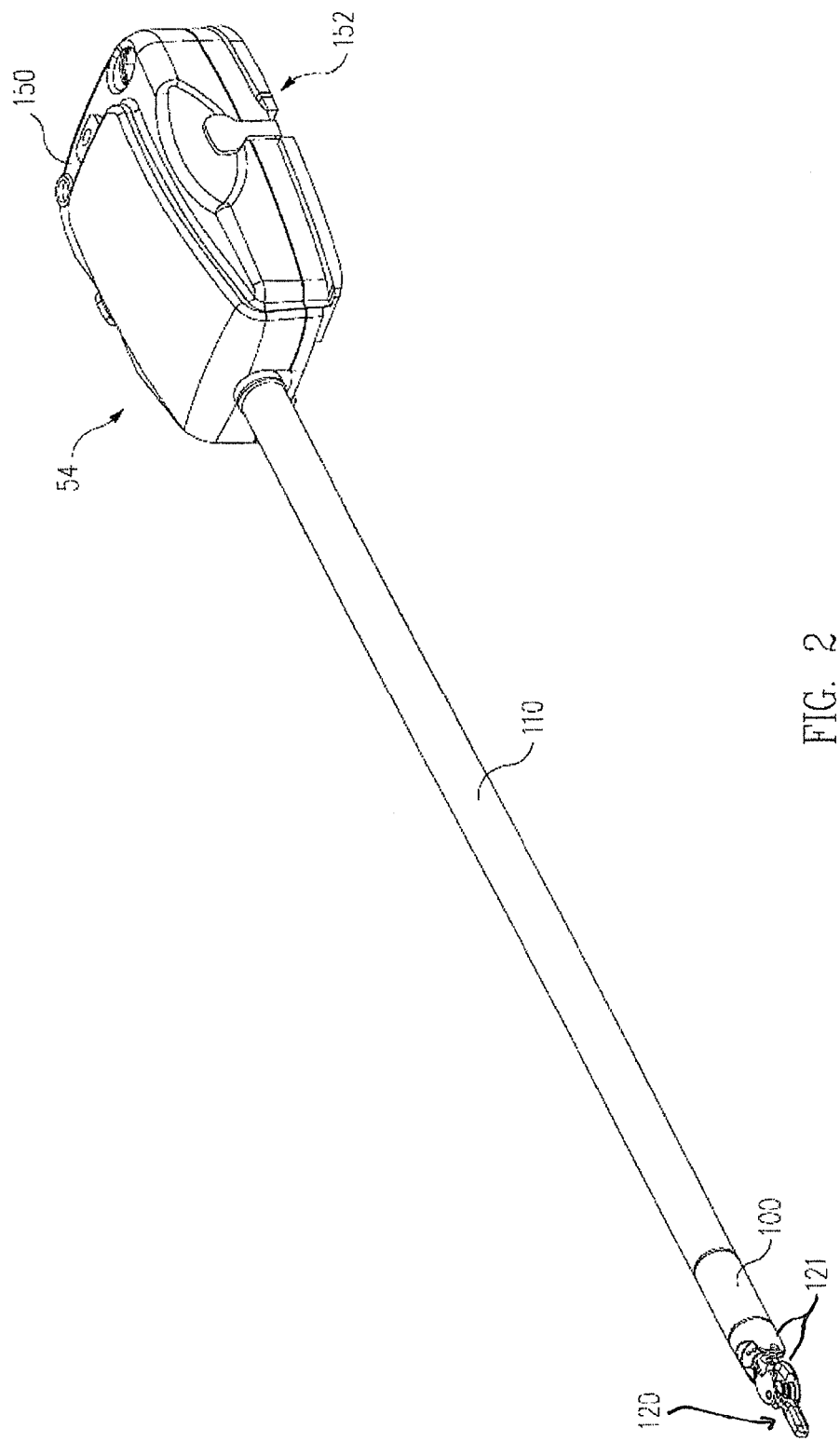
FIG. 2 is a perspective view of a surgical instrument including a force sensor apparatus operably coupled proximal (or inboard) to a wrist joint.

Referring to FIG. 2, a perspective view is shown of a surgical instrument 54 including a force sensor apparatus 100 operably coupled to a distal end of a rigid shaft 110 and proximal to a wrist joint 121 in accordance with an embodiment of the present invention. An end portion 120, such as a surgical end effector, is coupled to force sensor apparatus 100 via the wrist joint 121. A housing 150 is operably coupled to a proximal end of the rigid shaft 110 and includes an interface 152 which mechanically and electrically couples instrument 54 to the manipulator 51.

Housing 150 operably interfaces with a robotic manipulator arm 51, in one embodiment via a sterile adaptor interface. Applicable housings, sterile adaptor interfaces, and manipulator arms are disclosed in U.S. patent application Ser. No. 11/314,040 filed on Dec. 20, 2005, and U.S. application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

In a preferred configuration, end portion 120 has a range of motion that includes pitch and yaw motion about the x- and y-axes and rotation about the z-axis. These motions as well as actuation of an end effector are provided via cables in housing 150 and cables and/or rod linkages running through shaft 110 and into housing 150 that transfer motion from the manipulator arm 51. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

Figure 3A:
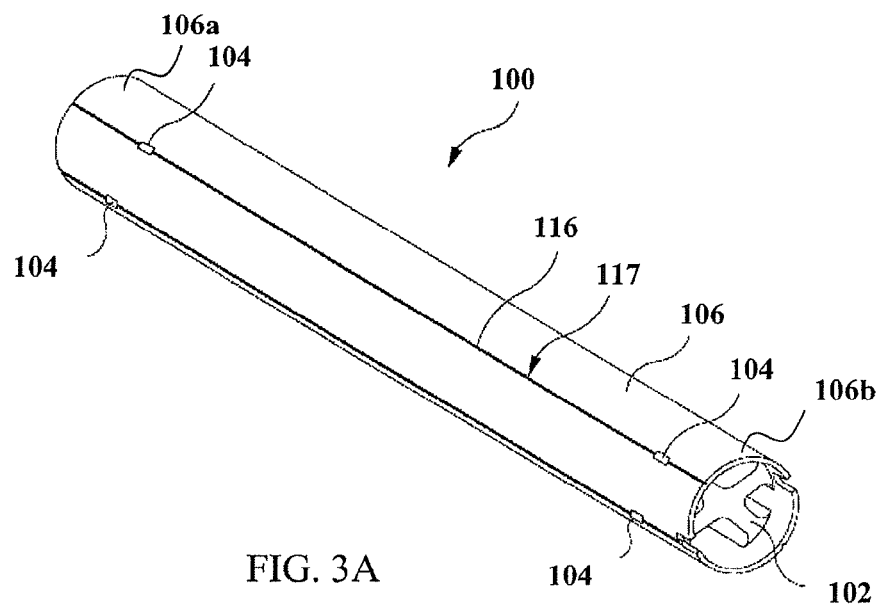
FIGS. 3A and 3B illustrate perspective views of a force sensor apparatus and an enlarged distal section of the force sensor apparatus, respectively.
Figure 3B:
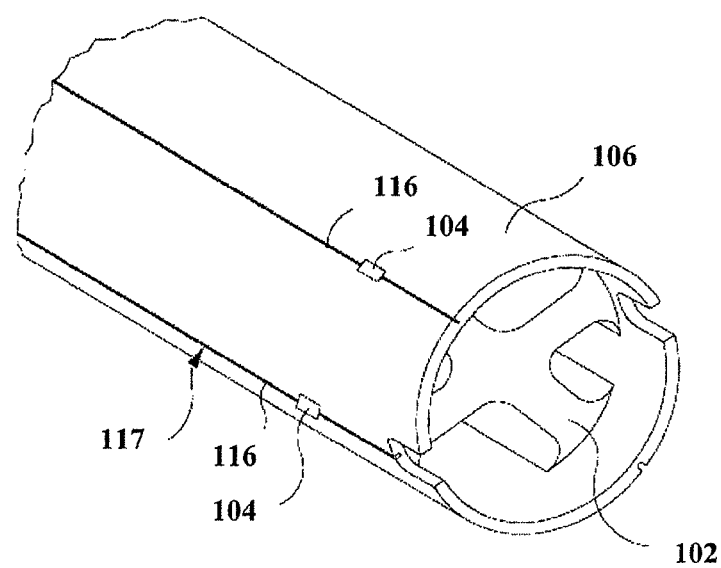
Figure 3C:
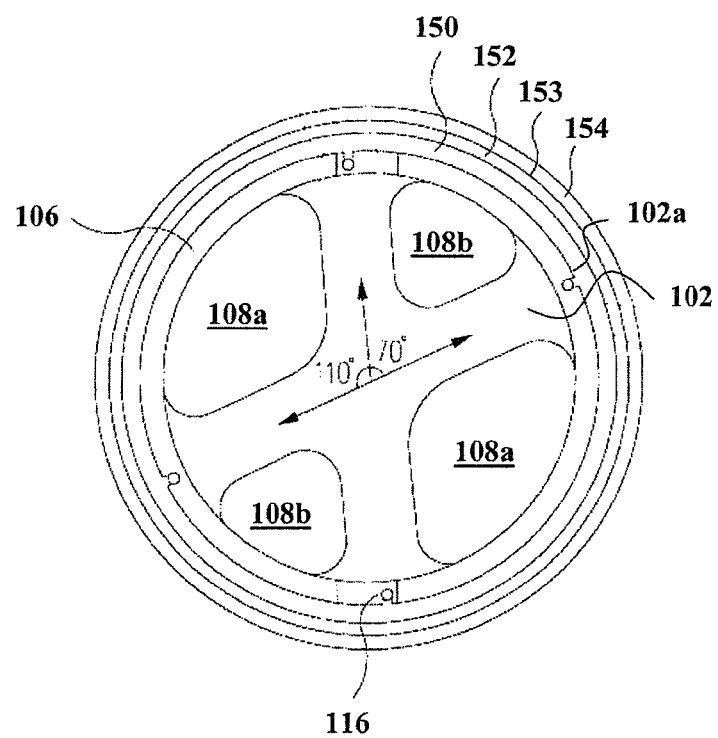
FIG. 3C illustrates an end view of the force sensor apparatus of FIGS. 3A and 3B including radial ribs positioned in non-uniform angles and thermal shielding layers over the sensor apparatus tube.

Referring now to FIGS. 3A-3C, a force sensor apparatus 100 is illustrated, the force sensor apparatus 100 including four ribs 102 in diametrically opposite pairs at skewed supplementary angles (e.g., 70 degrees and 110 degrees) about a z-axis centerline of a tube 106. Ribs 102 extend radially within tube 106 from the z-axis centerline of the tube providing four through passages 108a and 108b for passage of actuation cables, wires, tubes, and/or rods (which may be referred to as linkages), cautery wires and/or flushing liquids. Advantageously, a larger through passage 108a utilizing skewed angles allows for easier passage of cables, wires, tubes, and/or rods through tube 106 (e.g., three hypodermic tubes may be passed per 110 degree channel). As shown in FIG. 3A, tube 106 does not include apertures through the wall of tube 106. However, the combined stiffness of tube 106 and ribs 102 still allow for a strong strain signal to noise signal ratio consistent with a materials choice and rib design meeting the need for high thermal diffusivity and a direct thermal path between opposing strain gauges while also providing passage for actuation linkages.

Similar to the embodiments disclosed above, a number of strain gauges 104 are oriented parallel to the lengthwise z-axis of the tube and mounted to an outer rib surface 102a (FIG. 3C). The strain gauges may be inlaid into grooves or a depressed area 117 on the outer rib surface 102a in one example. Wire leads or optic fibers 116 (e.g., shielded twisted pairs, coax, or fiber) coupled to the strain gauges 104 may be inlaid into grooves 117 on the outer rib surface 102a of tube 106. The wire leads or optic fibers 116 may then be embedded in an adhesive potting compound such as epoxy.

Referring now in particular to FIG. 3C, an end view of force sensor apparatus 100 is illustrated. A thermal shielding may be provided over the strain gauges. In one example, a thermal shunt shell 152 is provided over tube 106 with an insulating fluid (gas or liquid) filled or evacuated gap 150 being provided between the outer surface of tube 106 and the inner surface of thermal shunt shell 152. Thermal shunt shell 152 may be comprised of a high thermal diffusivity material, such as an aluminum alloy (e.g., 6061-T6 aluminum) or a copper alloy (e.g., GlidCop® AL-60) or a silver alloy. Optionally, a light reflective surface or coating 153 may be provided over thermal shunt shell 152, which may deflect light and reduce localized heating of the force sensor apparatus, for example from endoscope illumination. An insulating coating 154 may also be provided over thermal shunt shell 152, the insulating coating 154 being comprised of a substantially transparent plastic shrink polymer in one example. Advantageously, the thermal shielding over the sensor tube 106 and the strain gauges 104 as described above allows for more uniform heat/thermal diffusion among the gauges, being particularly advantageous for mitigating asymmetric thermal loads upon the instrument. The thermal shielding described above is applicable for various embodiments of the present invention.

Force sensor apparatus 100 is a separately manufacturable module or part adapted for incorporation as part of the shaft 110 of surgical instrument 54 at a prescribed distance from the tip where there may be an articulated wrist with specialized jaws, cutting devices, or other end portion 120. Proximal tube portion 106a operably couples to the shaft 110 of surgical instrument 54 and distal tube portion 106b operably couples to a wrist joint 121. In one example, the diameter of the completed force sensor apparatus matches the diameter of the instrument shaft, thus allowing the entire assembly of the instrument (including the coupled force sensor apparatus) to pass through a cannula or a seal without added friction or snagging.

As disclosed in U.S. patent application Ser. No. 11/537, 241, filed Sep. 29, 2006, the contents of which have been previously incorporated by reference, strain gauges 104 may be spaced in a ring at intervals around the circumference of the tube 106 (e.g., 3 gauges at 120 degrees, 4 gauges at 90 degrees, or 4 gauges at 70 degrees and 110 degrees or other pairs of supplementary angles). The signals from the sensors are combined arithmetically in various sums and differences to obtain measures of transverse forces $F_x$ and $F_y$ (FIG. 3A) exerted upon the instrument tip and to reject axial force Fz and the torques Tx and Ty about the two axes perpendicular to the shaft axis (i.e., axes x and y). The measurement of the forces is made independent of the orientation and effective lever arm length of an articulated wrist mechanism 121 at the distal end of the instrument when two axially separated sets or rings of gauges are utilized and their signals are subtracted. Forces exerted against end portion 120 are detected by the force sensing elements via an interrogator, which may be operably coupled to the servo control or to a processor for notifying the surgeon of these forces (e.g., via master(s) or a display). It is understood that by adding a second ring of similarly oriented gauges (e.g., two sets of 3 gauges or two sets of 4 gauges) at a different lengthwise axial position on the tube, additional load-induced bending moment information may be obtained, and dependence of the transverse force data Fx, Fy on instrument wrist length, orientation, and resulting jaw distance may be eliminated.

In one example, various strain gauge types may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft for eight gauges.

Both fiber technologies require an interrogator unit that decodes the optically encoded strain information into electrical signals compatible with the computer control hardware or display means of the robotic surgical system. A processor may then be used to calculate forces according to the signals from the strain gauges/sensors.

Additionally, for resistive foil or semiconductor strain gauges there may be co-mounted unstrained gauges or Poisson strained gauges oriented in the circumferential direction adjacent to each axial gauge and incorporated in local bridge completion circuits to eliminate temperature effects. The strain gauge bridge circuits are completed in a manner to give the best signal for bending loads due to the lateral forces ($F_x$ and $F_y$) exerted on the instrument tip jaws.

Also for resistive foil or semiconductor strain gauges, active components such as bare die op-amps and passive components such as secondary resistors or capacitors may be attached adjacent to the strain gauges connected by bond wires or thick film circuit traces in the manner of hybrid circuits to amplify, filter, and/or modulate the gauge output signals to reject noise sources. Such components are not needed for fiber optic gauges.

For the methods and apparatus mentioned above, it may be advantageous to use a calibration process in which combinations of forces and torques are applied to the instrument tip serially or in simultaneous combinations while correction factors and offsets are determined. The correction factors and offsets may then be applied to the theoretical equations for combining the gauge outputs to obtain $F_x$, $F_y$, and reject $F_z$, $T_x$, and $T_y$. Such a calibration process may be done either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Advantageously, force sensor apparatus 100 is adaptable to the size and shape constraints of various robotic surgical instruments and is suitable for a variety of instruments. Furthermore, force sensor apparatus 100 may be manufactured, tested, and calibrated as a separate modular component and brought together with other components in the conventional instrument assembly process. Also, the sensor may be a slip-on module with suitable electrical or optical contacts that mate with contacts on the instrument shaft permitting a higher value sensor to be used with lower cost instruments of limited cycle life. In addition, the sensor structural member 106 may be comprised of an advantageous material, which may be the same or a different material than the instrument shaft 110 whose design considerations may compromise the properties required for the sensor.

Figure 4A:
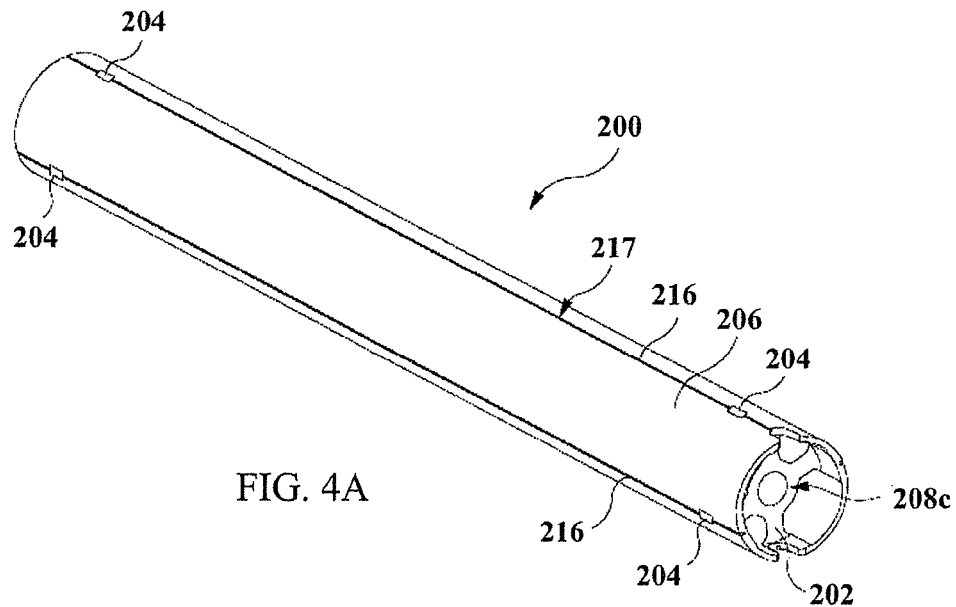
FIGS. 4A and 4B illustrate perspective views of another force sensor apparatus and an enlarged distal section of the force sensor apparatus, respectively.
Figure 4B:
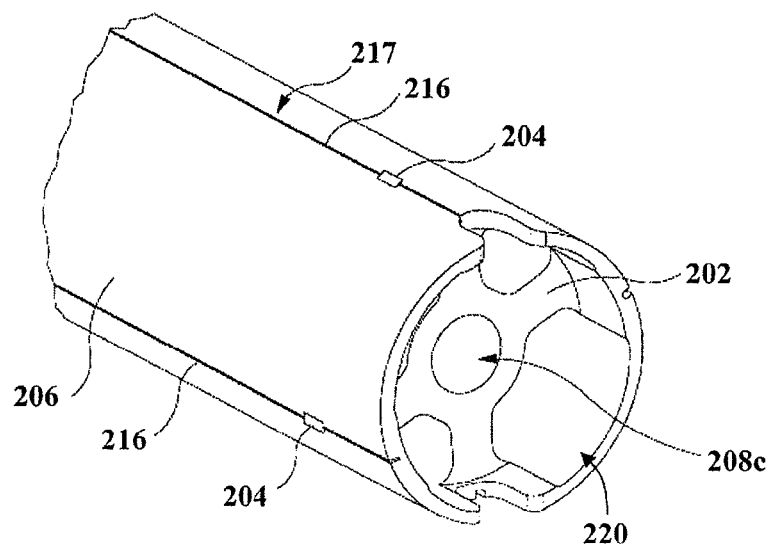
Figure 4C:
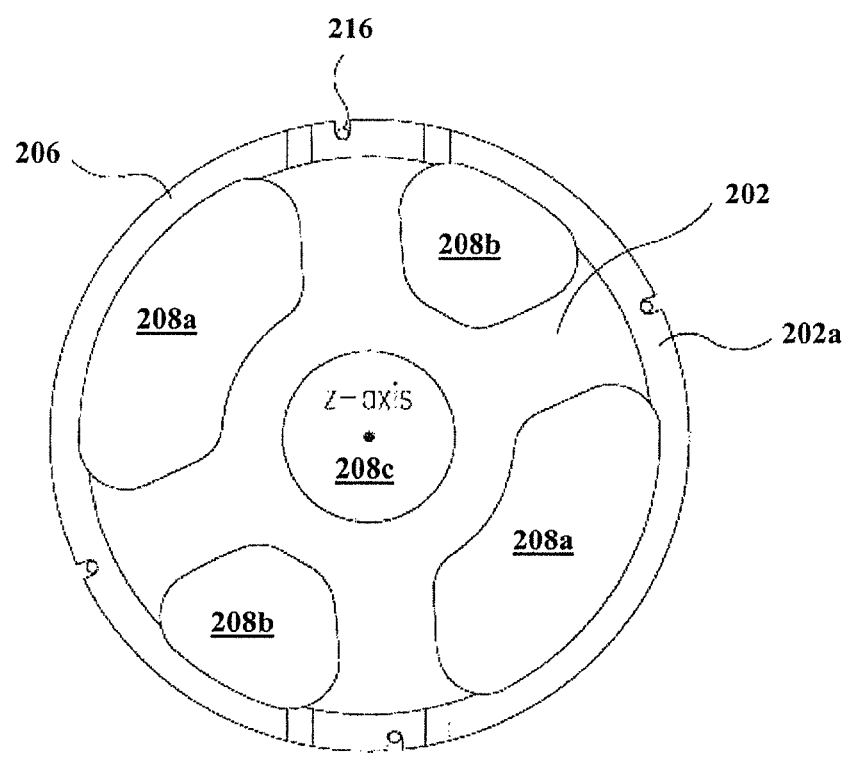
FIG. 4C illustrates an end view of the force sensor apparatus of FIGS. 4A and 4B including radial ribs positioned in non-uniform angles and a central through passage.

Referring now to FIGS. 4A through 4C, a force sensor apparatus 200 is illustrated in accordance with another embodiment. The descriptions of substantially similar parts or elements as those described above with respect to FIGS. 3A-3C are applicable in this embodiment with respect to FIGS. 4A-4D, and redundant descriptions may be omitted.

Force sensor apparatus 200 includes four ribs 202 paired at skewed angles (e.g., 70 degrees and 110 degrees or other pairs of supplementary angles) about a z-axis centerline of a tube 206. Ribs 202 extend radially within tube 206 from the z-axis centerline passage of the tube providing through passages 208a and 208b. In this embodiment, force sensor apparatus 200 also includes a central through passage 208c along a lengthwise axis z of tube 206 in accordance with another embodiment. The through passages may be used for passage of actuation linkages (e.g., cables, wires, tubes, and/or rods) and/or cleaning liquids. In this embodiment, the combined stiffness of tube 206 and ribs 202 allow for a strong strain signal to noise signal ratio consistent with a materials choice and rib design meeting the need for high thermal diffusivity and a thermal path between opposing strain gauges while also providing passage for actuation linkages and/or liquids.

Similar to the embodiments disclosed above, a number of strain gauges 204 are oriented parallel to the lengthwise z-axis of the tube and mounted to an outer rib surface 202a. The strain gauges may be inlaid into grooves or a depressed area 217 on the outer rib surface 202a in one example. Wire leads or optic fibers 216 (e.g., shielded twisted pairs, coax, or fiber) coupled to the strain gauges 204 may be inlaid into grooves 217 on the outer rib surface 202a of tube 206. The wire leads or optic fibers 216 may then be embedded in an adhesive potting compound such as epoxy.

Figure 5:
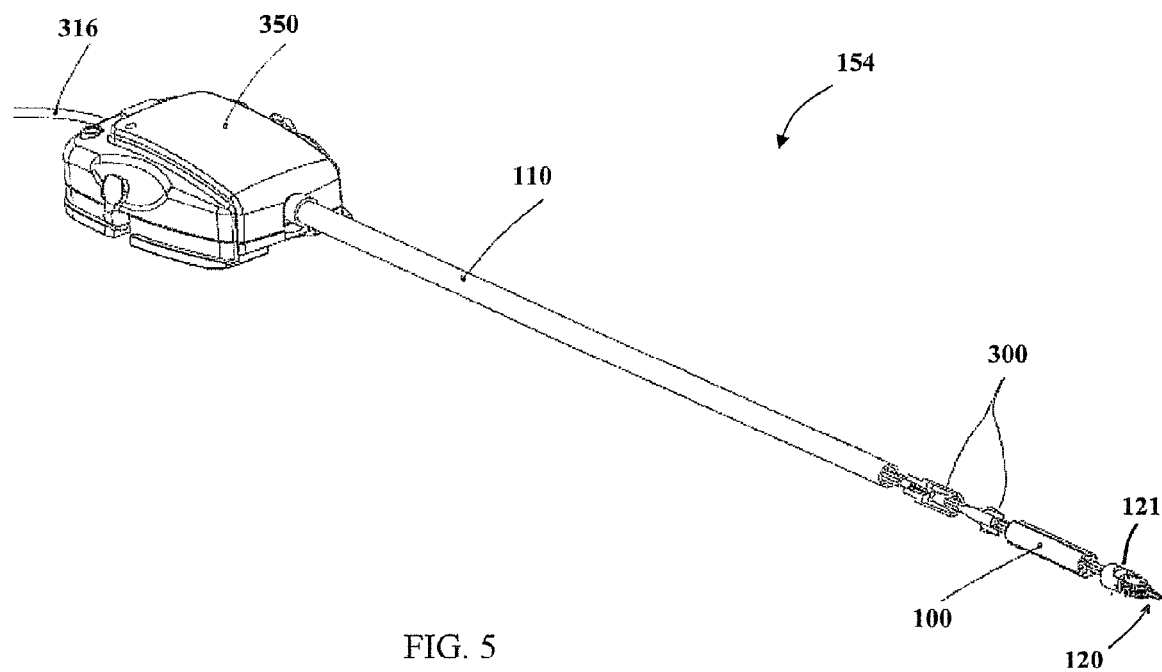
FIG. 5 illustrates a partial cut-out and exploded perspective view of a surgical instrument including a cleaning liquid flush manifold and a force sensor operably coupled proximal (or inboard) to a wrist joint in accordance with embodiments of the present invention.

Referring now to FIG. 5, a partial cut-out and exploded perspective view is illustrated of a surgical instrument 154 including a cleaning liquid flush manifold 300 and a force sensor 100 operably coupled proximal (or inboard) to a wrist joint in accordance with embodiments of the present invention. Instrument 154 further includes a housing 350 and optical fiber(s) running out of housing 350 through a sheath 316. Force sensor apparatus 100 may be exchanged with force sensor 200 in other embodiments, as will be later described.

Figure 6A:
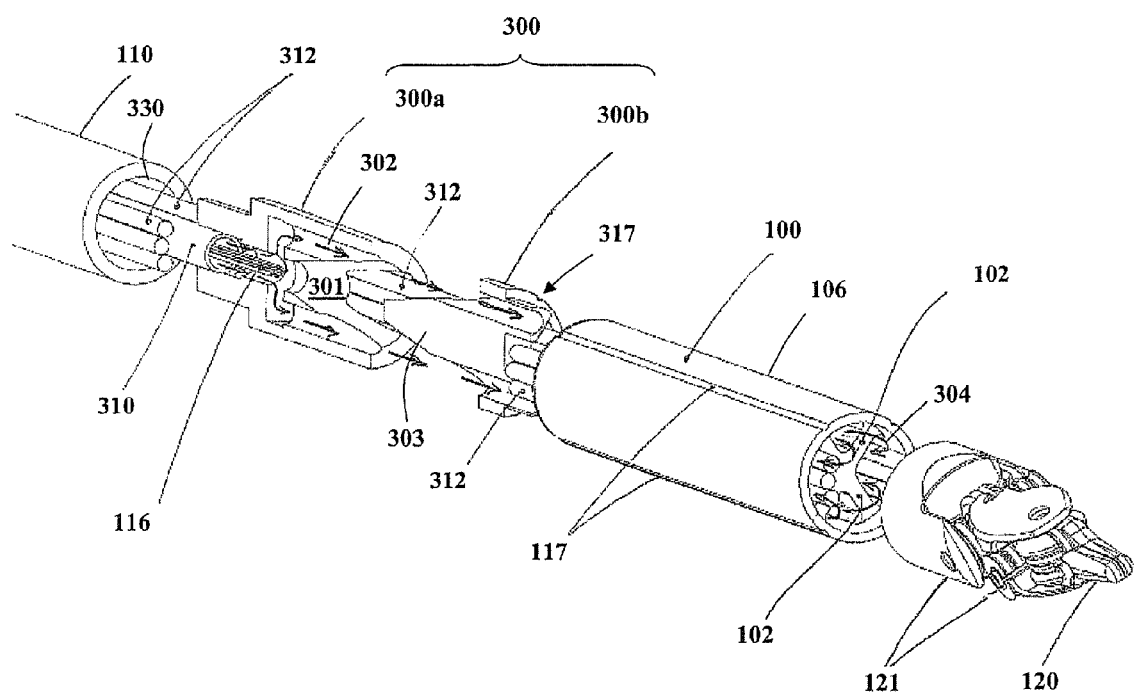
FIGS. 6A-6C illustrate enlarged perspective views of the manifold and force sensor of the instrument of FIG. 5 in accordance with embodiments of the present invention.
Figure 6B:
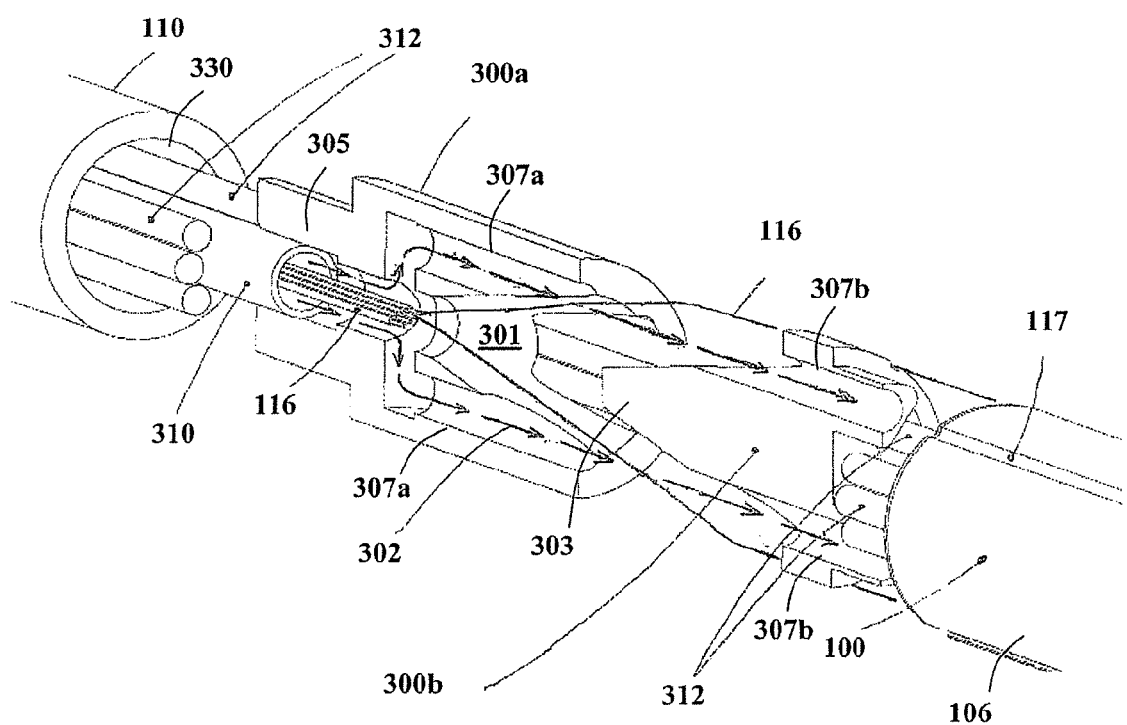
Figure 6C:
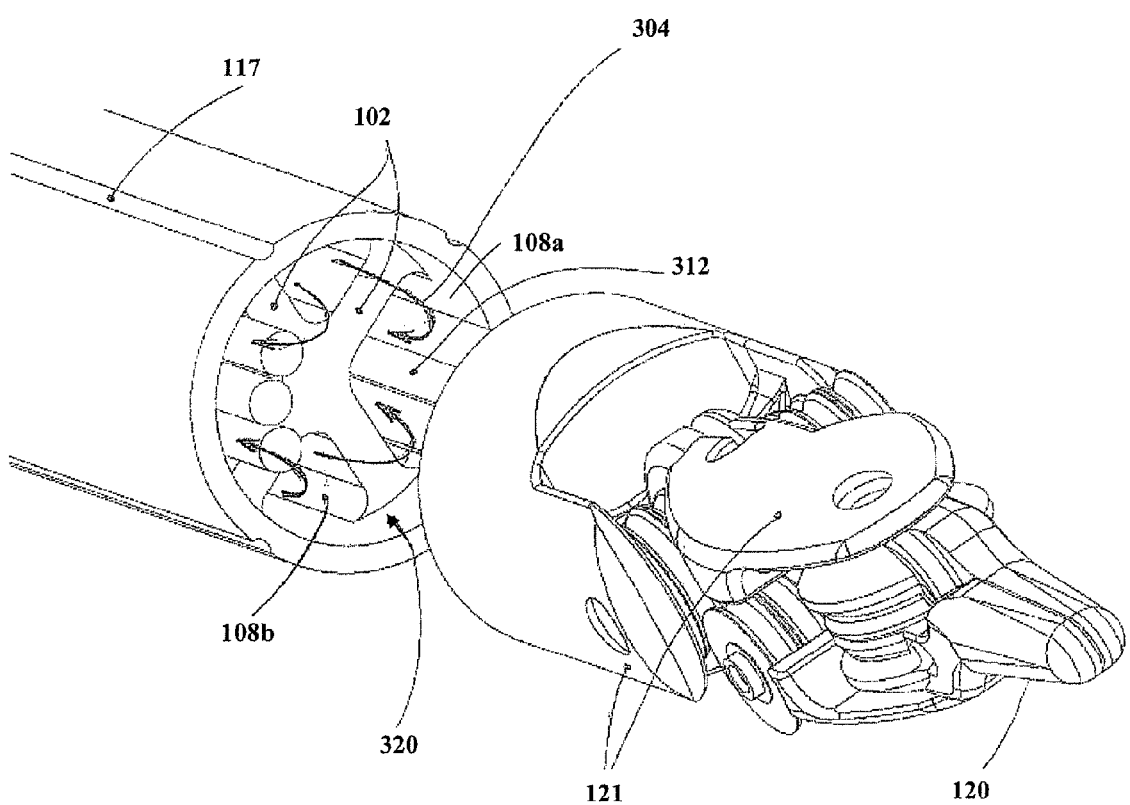

FIGS. 6A-6C illustrate enlarged perspective views of the manifold 300 and force sensor apparatus 100 of the instrument of FIG. 5 in accordance with embodiments of the present invention. As shown in FIGS. 6A-6C in conjunction with FIGS. 3A-3C, sensor apparatus 100 includes ribs 102 that form through passages 108a, 108b, and grooves 117 for placement or mounting of optical fibers 116. One set of ribs 102 are separated by 70 degrees and another set of ribs 102 are separated by 110 degrees, measured about the z-axis centerline of tube 106. Through passages 108a, 108b allow for passage of actuation linkages (e.g. cables, wires, tubes, rods), and/or cleaning liquids. In one example, through passages 108a provide a pathway for linkages such as cables, wires, tubes, and/or rigid tendons (rods) to pass through the sensor apparatus body to actuate the distal wrist joint(s) and/or control the end portion. Through passages 108a also provide a pathway for spent outbound redirected cleaning liquid while through passages 108b provide a pathway for inbound fresh cleaning liquid from a cleaning liquid supply, typically external to the instrument. A number (e.g., 3, 4, 6, or 8) of strain gauges are oriented parallel to the lengthwise z-axis of the tube and mounted to an outer rib surface. The strain gauges may be inlaid into grooves or a depressed area 117 on the outer rib surface in one example.

In one example, tube 106 and ribs 102 may be made of similar materials as described above with respect to other embodiments. Advantageously, the present invention allows for a low bending moment of inertia to increase a strain signal to noise signal ratio consistent with a materials choice and rib design meeting the need for high thermal diffusivity and a direct thermal path between opposing strain gauges while also providing passage for actuation cables, wires, tubes, rods, and/or cleaning liquids.

Force sensor apparatus 100 has been described above with respect to FIGS. 3A-3C and redundant descriptions will be omitted although the descriptions of substantially similar parts or elements as those described above with respect to FIGS. 4A-4C are applicable in this embodiment.

Flush manifold 300 is positioned between instrument shaft 110 and force sensor apparatus 100 or inside of shaft 110 and is operably coupled to a central flush supply tube 310 running through the center of shaft 110, which creates an annulus 330 (FIGS. 6A-6B) between an outer surface of flush supply tube 310 and an inner surface of shaft 110. Linkages 312 and spent outbound cleaning liquid pass through annulus 330 inside shaft 110 and outside supply tube 310. In accordance with the present invention, flush supply tube 310 originates at the instrument housing 150 and passes in the distal direction between linkages (e.g., wrist actuation tendons) toward the proximal portion of manifold 300 and the force sensor apparatus 100 for supplying cleaning liquid.

Flush manifold 300 directs cleaning liquid from flush supply tube 310 into the through passages of the force sensor apparatus 100, as shown by arrows 302 (FIGS. 6A-6B, 7A, and 7D-7E). In one embodiment, flush manifold 300 directs cleaning liquid from flush supply tube 310 to through passages 108b of sensor apparatus 100 (FIG. 6C) and proximal to wrist 121. In one embodiment, the cross-sectional areas of the through passages 108b are substantially equal, and thus the flow volume, rate, and cleaning power of the cleaning liquid within each of the through passages 108b is substantially equal, insuring equal cleaning of the pairs of diametrically opposite through passages.

A plenum zone 320 (FIG. 6C) at a distal end of tube 106 of force sensor 100 allows for collecting cleaning liquid from through passages 108b and redirecting the cleaning liquid to other through passages in the force sensor apparatus. In one embodiment, plenum zone 320 collects fresh cleaning liquid from through passages 108b, cleans exposed proximal surfaces of the wrist 121, and then redirects the cleaning liquid back toward the proximal end of tube 106 via through passages 108a and along the linkages 312. The redirected cleaning liquid from the plenum zone 320 then flows along linkages 312 running next to manifold 300 and finally along linkages 312 running through annulus 330 inside shaft 110, finally exiting the instrument through housing 150. In one embodiment, the plenum zone redirects the cleaning liquid flowing at a velocity sufficient to clean the linkages 312.

Figure 7A:
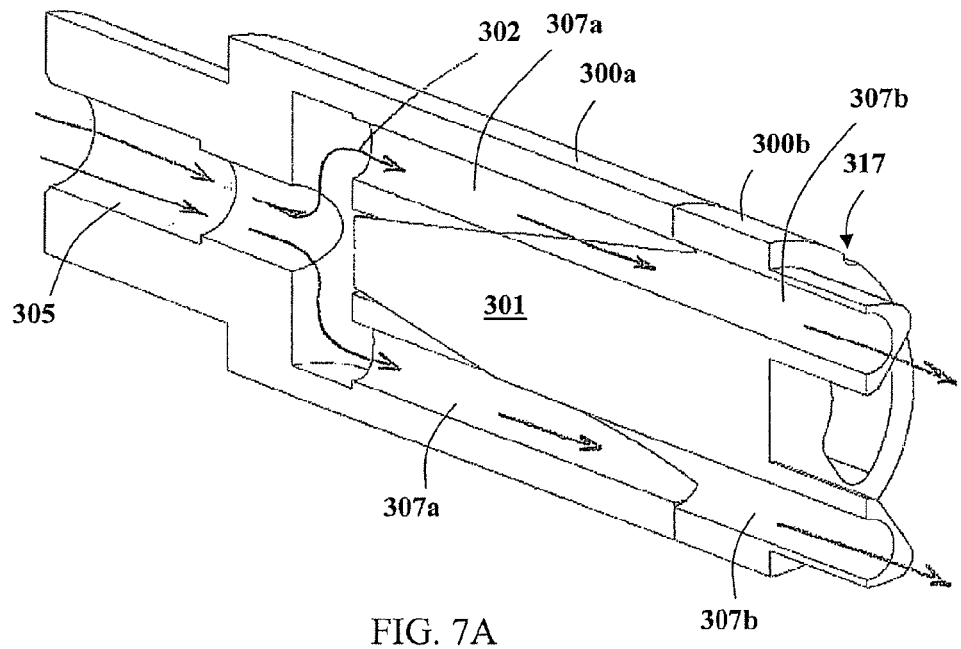
FIGS. 7A-7F illustrate views of the flush manifold in accordance with embodiments of the present invention.
Figure 7B:
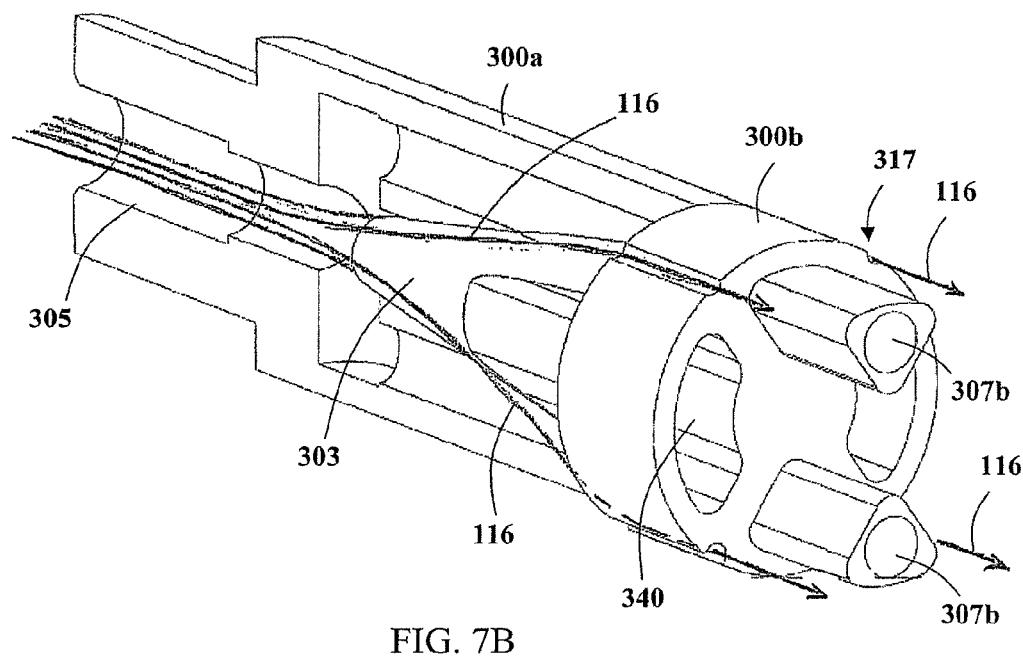
Figure 7C:
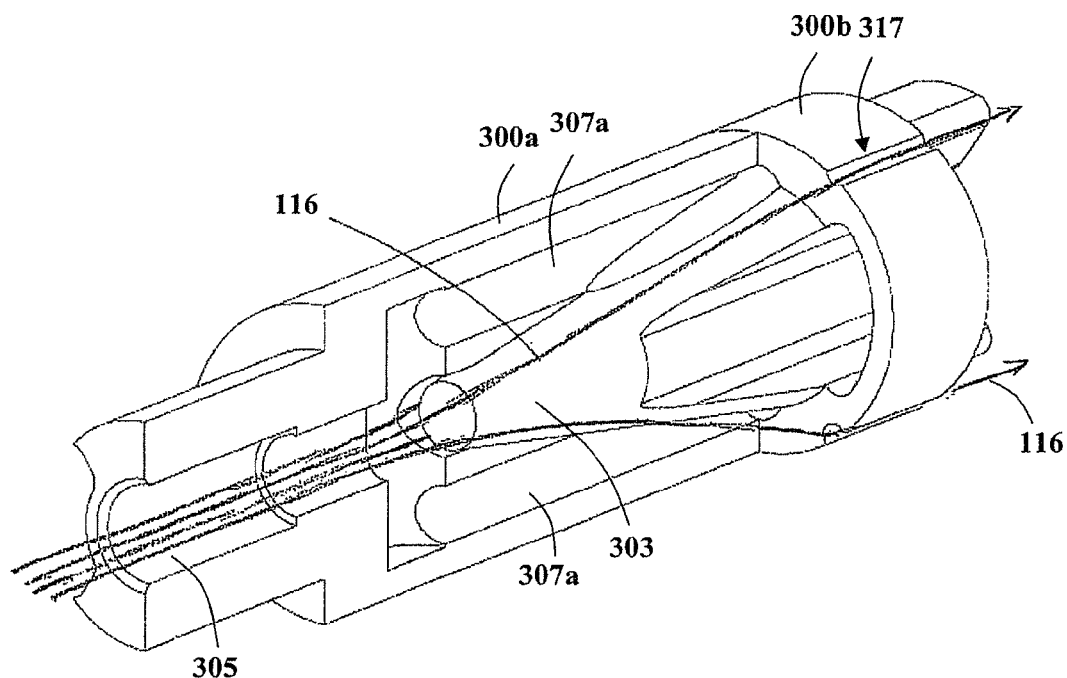
Figure 7D:
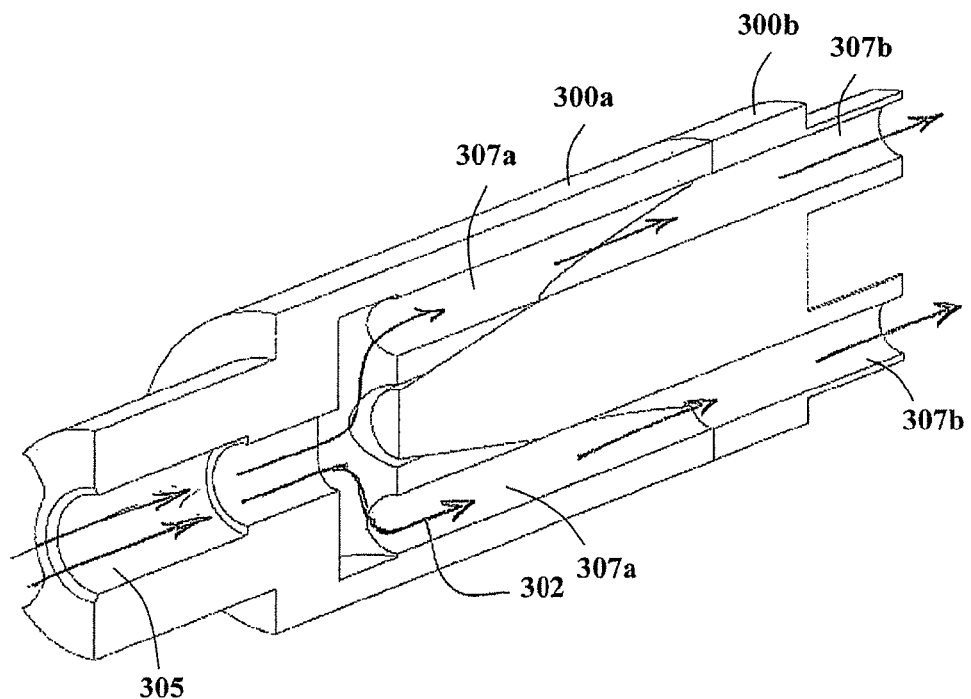
Figure 7E:
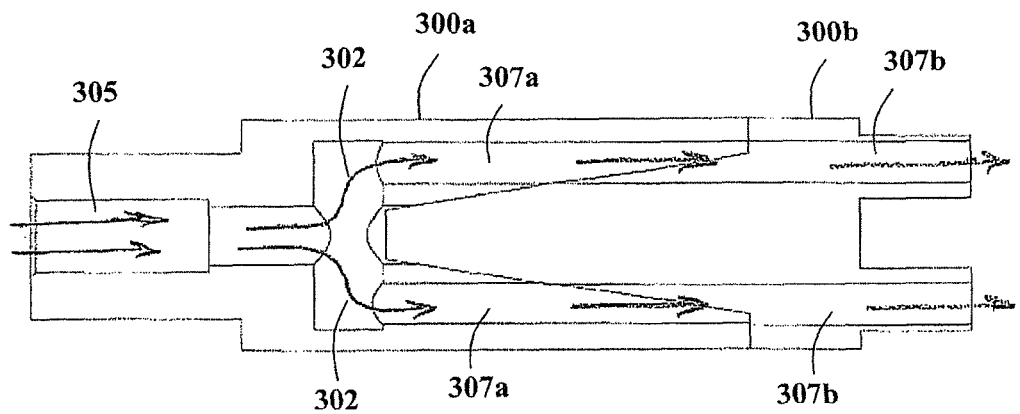
Figure 7F:
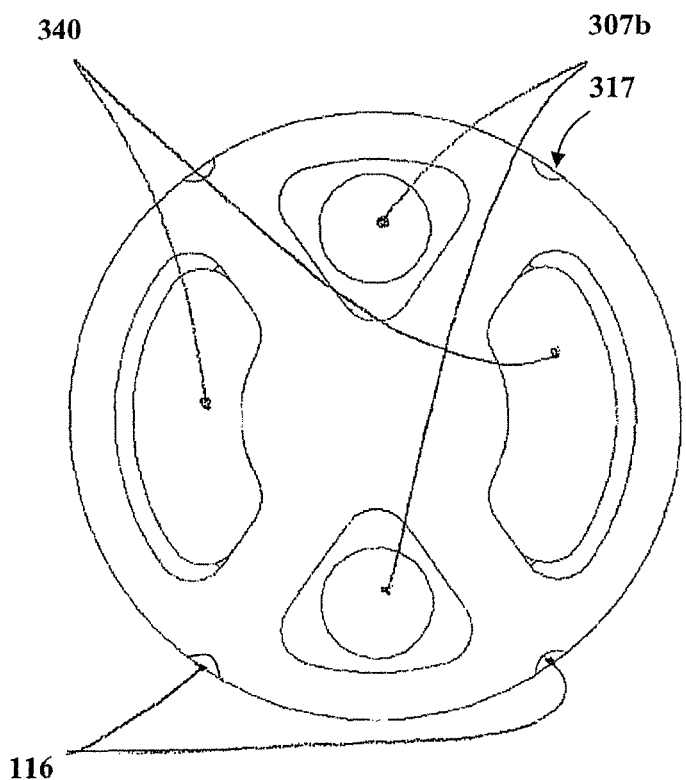

Referring now to FIGS. 7A-7F in conjunction with FIGS. 6A-6C, different views of flush manifold 300 are illustrated and will be further described. FIGS. 7A and 7D illustrate sectional views of an assembled flush manifold 300 including a first manifold 300a and a second manifold 300b. FIGS. 7B and 7C illustrate perspective views of the second manifold 300b mated with the first manifold 300a shown in a sectional perspective view. FIG. 7E illustrates a sectional side view of mated manifold 300, and FIG. 7F illustrates a distal end view of manifold 300.

First manifold 300a includes a tapered opening 301 for receiving a mating tapered protrusion 303 of second manifold 300b. First manifold 300a further includes an inlet 305 for receiving flush supply tube 310 and two outlets 307a that split the incoming cleaning liquid from flush supply tube 310. In one embodiment, inlet 305 may include a female conical guide surface that allows for operable coupling to flush supply tube 310 in a blind manner with minimal flow loss. Outlets 307a are operably coupled to outlets 307b of second manifold 300b when the first and second manifolds are operably mated. Outlets 307b are operably coupled to through passages 108b of the sensor apparatus 100, thus allowing cleaning liquid to pass from flush supply tube 310 to through passages 108b in a balanced manner.

In one embodiment, optic fibers 116 run through flush supply tube 310 and then between first manifold 300a and second manifold 300b to respective grooves 317 on the outer surface of second manifold 300b. Grooves 317 align with grooves 117 on tube 106 of sensor apparatus 100. The layout of two optic fibers 116 are illustrated in FIGS. 6B and 7C for clarity of the illustration although all four optic fibers run to respective grooves 317 on the outer surface of manifold 300b (FIG. 7B). The optic fibers 116 may run along grooves in the interior surface of first manifold 300a and/or along grooves on the exterior surface of protrusion 303 of second manifold 300b in one embodiment. In another embodiment, the fibers may follow an S-shaped path in grooves between the manifold halves insuring minimum bending stress in the fibers as they transition from near the centerline to the grooves 117 on the outer surface of transducer 100. In yet another embodiment, the gap or grooves through which the fibers pass between the manifold halves are sealed to prevent leakage of flow intended to reach passages 108b in transducer 100.

FIG. 7F illustrates a distal end view of second manifold 300b, and in particular shows outlets 307b through which fresh cleaning liquid may flow, and passages 340 through which actuation linkages may run.

Figure 8A:
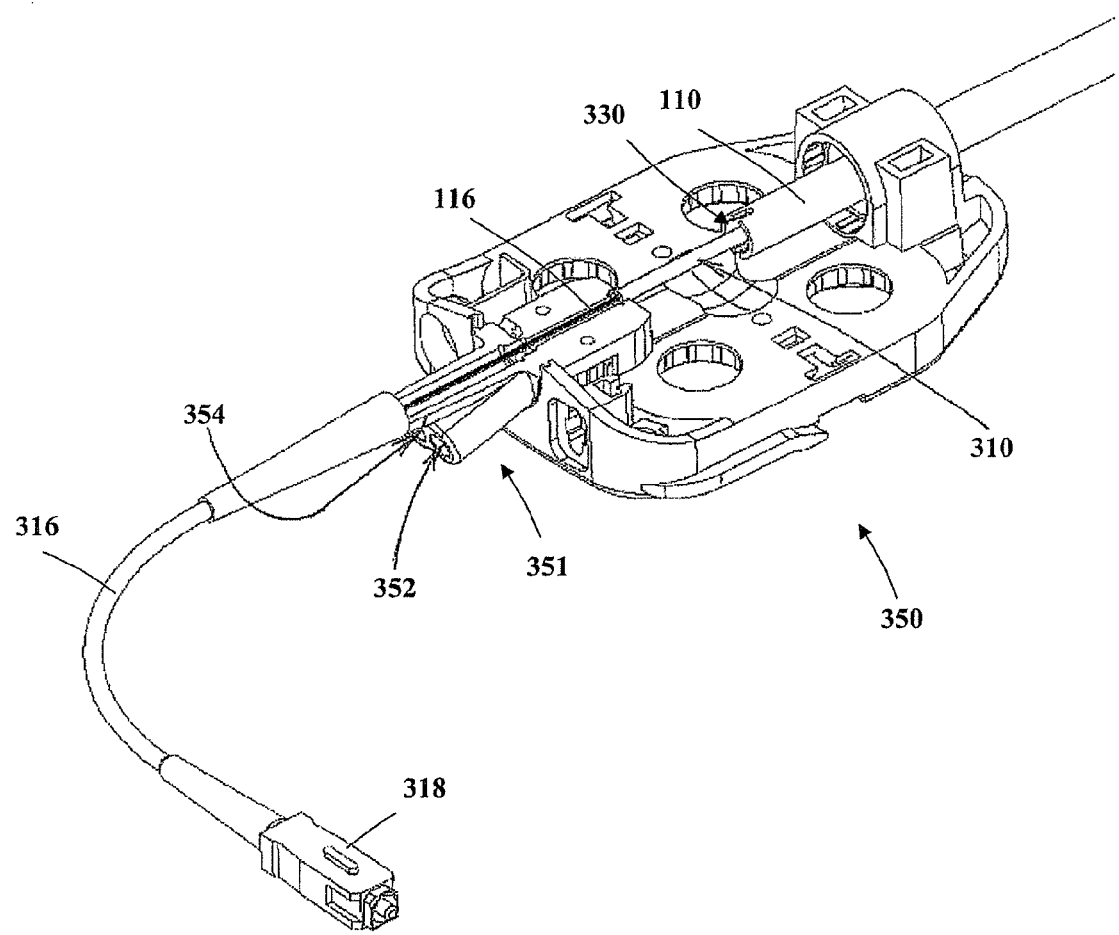
FIGS. 8A-8C illustrate partial cut-out and enlarged perspective views of the instrument housing section (without a housing cover) of the instrument of FIG. 5 in accordance with embodiments of the present invention.
Figure 8B:
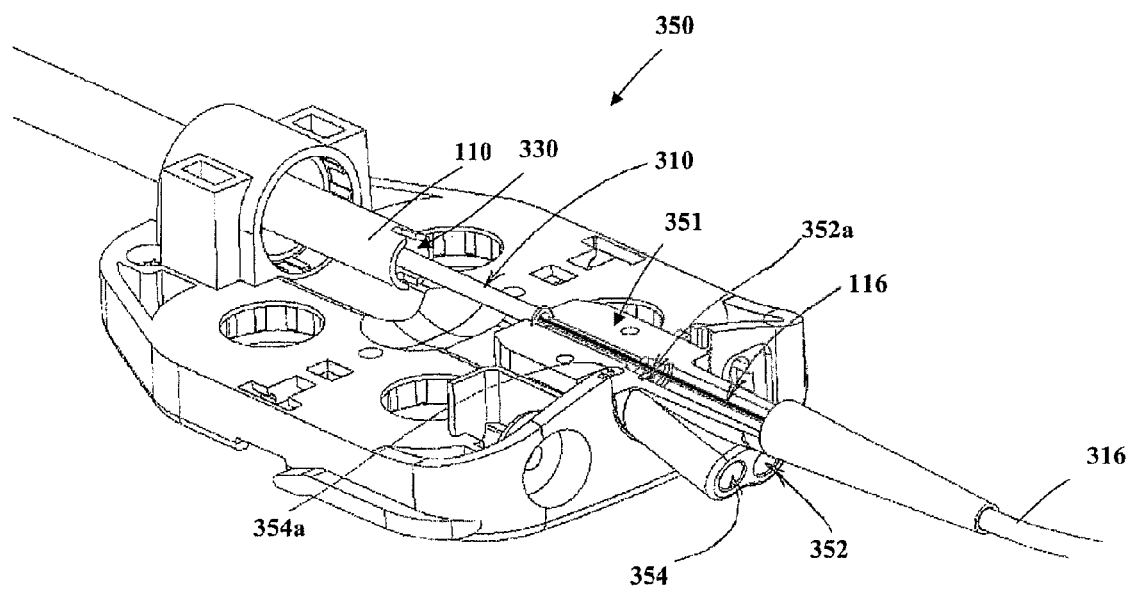
Figure 8C:
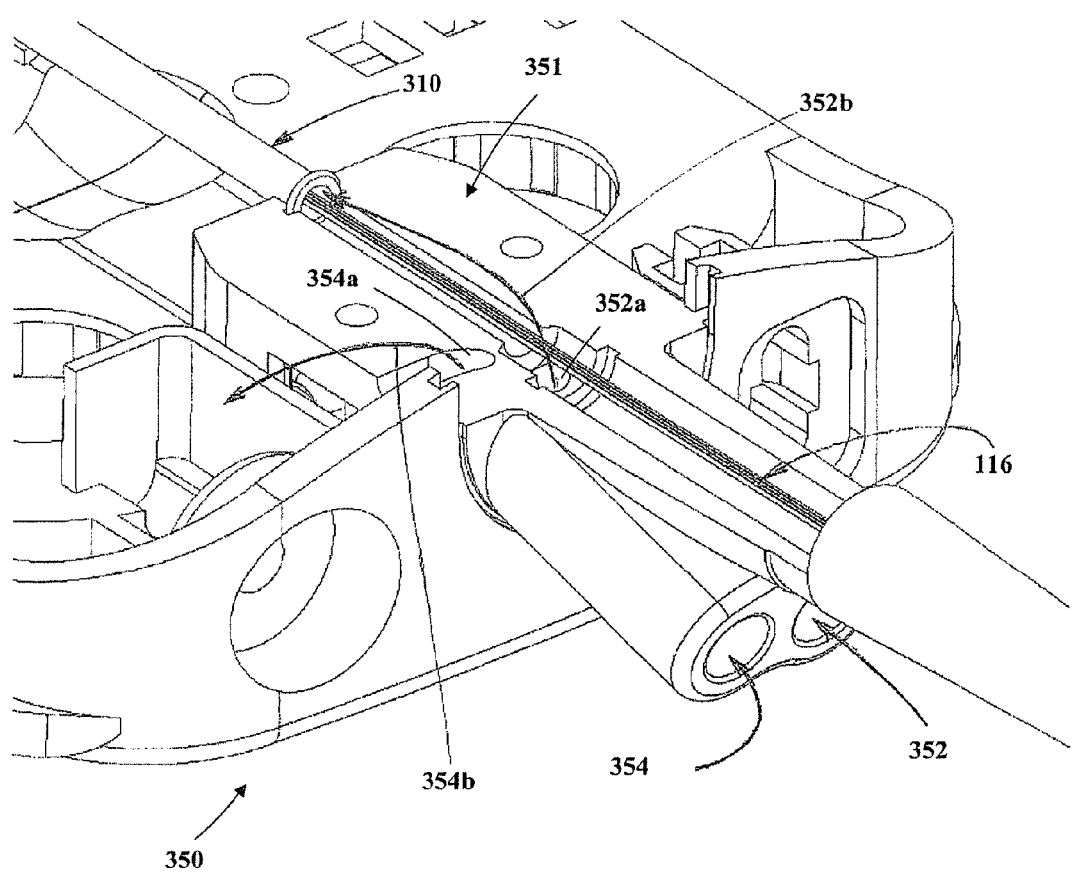

Referring now to FIGS. 8A-8C, partial cut-out and enlarged perspective views are illustrated of the instrument housing section (without a housing cover) of the instrument 154 of FIG. 5 in accordance with embodiments of the present invention. Flush supply tube 310 runs from a port block 351 (shown without a port block cover), through shaft 110, and ends at manifold 300 in one embodiment. Port block 351 includes a first Luer port 352 for injecting cleaning liquid to be flowed through flush supply tube 310 and a second Luer port 354 for injecting cleaning liquid to clean housing 350. Liquid injected through first port 352 exits at aperture 352a and continues to flush supply tube 310 as shown by arrow 352b (FIG. 8C) returning to the instrument housing 350 through annulus 330 (FIGS. 8A and 8B). Liquid injected through second port 354 exits at aperture 354a and spreads through the rear housing as shown by arrow 354b (FIG. 8C). A port block cover is mounted over the section of port block 351 shown such that flush flow 352b and fibers 116 are passed through port block 351 within a substantially sealed port block passage to the centerline flush supply tube 310. Accordingly, flush liquid from Luer port 352 to supply tube 310 will not leak out of port block 351.

In one embodiment, as shown in FIG. 8A, optical fibers 116 running through flush supply tube 310 pass out of port block 351 and housing 350 through a sheath 316 and end at an optical connector 318, an example of which is described in U.S. application Ser. No. 12/415,795, filed Mar. 31, 2009, the disclosure of which is incorporated by reference herein for all purposes.

It is noted that various cleaning liquids may be used within the scope of the present invention, such as recommended dilutions of Alconox Tergazyme or Ruhof Endozime.

Similar to the embodiments described above, the housing operably interfaces with a robotic manipulator arm, in one embodiment via a sterile adaptor interface. Applicable housings, sterile adaptor interfaces, and manipulator arms are disclosed in U.S. patent application Ser. No. 11/314,040 filed on Dec. 20, 2005, and U.S. patent application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

As previously noted above, sensor apparatus 100 can be exchanged with sensor apparatus 200 but in this case the manifold is replaced by a similar adapter that separates the optic fibers from the liquid flow so that the fibers may pass outward to grooves 217 of force sensor 200. Cleaning liquid from flush supply tube 310 may then flow through central through passage 208c (FIGS. 4A-4C) and plenum zone 220 (FIG. 4B) at a distal end of tube 206 of force sensor 200 may redirect the cleaning liquid to through passages 208a and 208b (FIGS. 4A-4C). The redirected cleaning liquid from the plenum zone 220 then flows along and cleans linkages 312 running through either of passages 208a, 208b, along linkages 312 running through annulus 330 inside shaft 110, and finally exits the instrument through housing 150.

Advantageously, the combination of the flush tube, flow directing manifold, and sensor through passages insures that cleaning liquid reaches the distal end of the force sensor apparatus and the proximal face of wrist 121 and returns by a different path providing for removal of liquids and debris that may have entered the sensor or instrument tube during surgery and which would otherwise compromise the cleanliness and sterilization of the instrument needed prior to use. In particular, the present invention allows for cleaning of contaminant entry and accumulation areas and the linkages of the instrument.

It is noted that various surgical instruments may be improved in accordance with the present invention, including but not limited to tools with and without end effectors, such as jaws, scissors, graspers, needle holders, microdissectors, staple appliers, tackers, suction irrigation tools, clip appliers, cutting blades, hooks, sealers, lasers, irrigators, catheters, and suction orifices. Alternatively, the surgical instrument may comprise an electrosurgical probe for ablating, resecting, cutting or coagulating tissue. Such surgical instruments are manufactured by Intuitive Surgical, Inc. of Sunnyvale, Calif.

Embodiments described above illustrate but do not limit the invention. It should also be understood that numerous modifications and variations are possible in accordance with the principles of the present invention. For example, the number of strain gauges and their configuration may vary but must allow for applicable transverse force determinations and wrist joint friction and actuator cable tension noise rejection. Similarly, the present invention is not limited to rib orientation or a certain number of ribs, sets of ribs, or strain gauges, and the number of ribs and angle between ribs may vary from those described above. Furthermore, the embodiments of force sensor apparatus described above may be integrated with a surgical instrument upon manufacture as a non-separable part of the shaft. Accordingly, the scope of the invention is defined by the following claims.

I claim:

1. A surgical instrument comprising:
   an instrument shaft having a first end oriented in a first direction and a second end oriented in a second direction opposite the first direction;
   one or more linkages passing through the instrument shaft; and
   a cleaning part configured to clean the or each of the one or more linkages, the cleaning part comprising:
     a flush manifold in the instrument shaft, the flush manifold being configured to receive a liquid;
     a passage through the instrument shaft, the passage having a first end oriented in the first direction and a second end oriented in the second direction, the first end of the passage being coupled to the flush manifold to receive the liquid from the flush manifold; and
     a plenum coupled to the second end of the passage to receive the liquid from the passage, the plenum being configured to redirect the received liquid toward the first end of the instrument shaft.

2. The surgical instrument of claim 1, wherein the passage comprises a through passage formed by a plurality of radial ribs.

3. The surgical instrument of claim 2;
   wherein the passage is included in a plurality of passages coupled to the flush manifold; and wherein the flush manifold is configured to direct substantially equal flow volumes of the liquid to each of the plurality of passages.

4. The surgical instrument of claim 1, further comprising: a housing coupled to the first end of the instrument shaft.

5. The surgical instrument of claim 4, the housing comprising a flushing block configured to admit an optical fiber into the instrument shaft, wherein the flushing block comprises a first port coupled to the instrument shaft and configured to direct the liquid to the flush manifold.

6. The surgical instrument of claim 5, wherein the flushing block comprises a second port configured to direct the liquid to an interior of the housing.

7. The surgical instrument of claim 4 further comprising: a tube within the instrument shaft, the tube being coupled to the flush manifold to supply the liquid to the flush manifold, and the tube being configured to permit passage of the liquid and an optical fiber through the tube.

8. The surgical instrument of claim 1, wherein the flush manifold is configured to separate an optical fiber from the liquid.

9. The surgical instrument of claim 1, wherein the flush manifold includes at least an aperture configured to receive the liquid redirected from the plenum.

10. The surgical instrument of claim 1, further comprising:
a wrist mechanism coupled to the second end the instrument shaft; and
an end effector coupled to the wrist mechanism.

11. The surgical instrument of claim 10, wherein the wrist mechanism is coupled to a first actuating mechanism by a first one of the one or more linkages, and the end effector is coupled to a second actuating mechanism by a second one of the one or more linkages.

12. The surgical instrument of claim 1, the passage being a central through passage of the instrument shaft.

13. The surgical instrument of claim 1, further comprising a liquid supply port coupled to the flush manifold.

14. The surgical instrument of claim 1, further comprising an end effector coupled to the second end of the instrument shaft.

15. The surgical instrument of claim 1:
wherein the passage is included in a plurality of passages coupled to the flush manifold; and
wherein the flush manifold is configured to direct substantially equal flow volumes of the liquid to each of the plurality of passages.

16. The surgical instrument of claim 1, the plenum being configured to redirect the received liquid toward the first end of the instrument shaft along the one or more linkages.

* * * * *